(12) United States Patent
Ou-Yang et al.

(10) Patent No.: US 7,601,959 B2
(45) Date of Patent: Oct. 13, 2009

(54) THIN TYPE VACUUM CHAMBER DEVICE

(75) Inventors: Mang Ou-Yang, Jhongli (TW);
Tzong-Sheng Lee, Jhongli (TW);
Ming-Hua Chang, Jhongli (TW)

(73) Assignee: National Central University, Taoyuan County (TW)

( * ) Notice: Subject to any disclaimer, the term of this patent is extended or adjusted under 35 U.S.C. 154(b) by 0 days.

(21) Appl. No.: 12/007,906

(22) Filed: Jan. 17, 2008

(65) Prior Publication Data

US 2009/0184248 A1   Jul. 23, 2009

(51) Int. Cl.
*G01J 5/02* (2006.01)
(52) U.S. Cl. ...................................... 250/343
(58) Field of Classification Search ................. 250/343, 250/352, 428, 338.1; 219/121.83, 121.84, 219/121.86; 315/500
See application file for complete search history.

(56) References Cited

U.S. PATENT DOCUMENTS 5,816,052 A * 10/1998 Foote et al. .................. 62/51.1
6,144,031 A * 11/2000 Herring et al. ............... 250/352

* cited by examiner

*Primary Examiner*—David P Porta
*Assistant Examiner*—Faye Boosalis
(74) *Attorney, Agent, or Firm*—Rosenberg, Klein & Lee

(57) ABSTRACT

The present invention is to provide a thin type vacuum chamber device, wherein two hollow slabs are fastened by a claw fastener to form a thin type simple structure that can maintain a high vacuum state, and wherein the air inside the chamber is pumped out to attain a vacuum state with a high pressure suction activity. The thin-chamber design of the present invention can decrease the number of the components and reduce the cost. The special assembly design of the vacuum chamber of the present invention can effectively decrease the length of the transmission cable and thus can reduce signal attenuation and noise interference. The present invention has the advantage of convenient operation and is very suitable to a two-dimensional infrared sensor.

7 Claims, 2 Drawing Sheets

THIN TYPE VACUUM CHAMBER DEVICE

BACKGROUND OF THE INVENTION

1. Field of the Invention

The present invention relates to a vacuum chamber device, particularly to a thin type vacuum chamber device.

2. Description of the Related Art

In modern science and technology, the vacuum device plays an important role in many fields, for example, the fields of film plating, testing, analysis and fabrication. The conventional vacuum chamber has many components, which increase fabrication complexity, prolong vacuum pumping time, and raise cost. Besides, the vacuum chamber likely to maintain the high vacuum state usually has a lager volume. Thus, the elements fabricated or tested in the vacuum chamber have poor optical communication with the exterior. Further, placing sensors or replacing damaged components is usually very hard in the conventional vacuum chamber. Furthermore, the conventional vacuum chamber usually has too long a focal length of the lens of the optical system, which influences the quality. Besides, the conventional vacuum chamber usually has too long a signal transmission cable, and signals are thus apt to be interfered and attenuated. Moreover, the sensors inside the conventional vacuum chamber are unlikely to be heated from the exterior, which usually causes operational troubles. In conclusion, the abovementioned disadvantages not only give inconvenience to users but also bring difficulty to the maintenance personnel.

Therefore, the present invention proposes a thin type vacuum chamber device to overcome the abovementioned problems.

SUMMARY OF THE INVENTION

The primary objective of the present invention is to provide a thin type vacuum chamber device, which can maintains a high vacuum state, wherein a high pressure air suction activity draws away the air inside the chamber to attain a vacuum state. Therefore, the thin type vacuum chamber device of the present invention can be effectively applied to sensors, such a two-dimensional infrared sensor.

Another objective of the present invention is to provide a thin type vacuum chamber device, wherein the back focal length of the lens of the test system is reduced, which cooperates with the conduction design and the chamber design to reduce the length of the signal transmission cable and thus decrease the noise interference and signal attenuation.

Further objective of the present invention is to provide a thin type vacuum chamber device, wherein the sensors inside the vacuum chamber can be directly heated from the exterior of the chamber, which conveniences operation and control.

To achieve the abovementioned objectives, the present invention proposes a thin type vacuum chamber device, which comprises: a chamber, a rotary claw fastener, two rotary spindle valves, a window and a signal transmission device. The chamber includes two hollow slabs. The rotary claw fastener is arranged on the top of the chamber and tightly fastens the two hollow slabs. The two rotary spindle valves are respectively arranged at two sides of the chamber, wherein the left vacuum spindle valve is an outlet through which the air inside the chamber is pumped out to attain a vacuum state, and the right vacuum spindle valve is used in inspecting the vacuum state. The window allows light to enter the chamber and focus over there. The signal transmission device includes a conduction device and a transmission cable and is used to send signals to the exterior.

Below, the embodiments are described in detail in cooperation with the drawings to make easily understood the objectives, technical contents, characteristics and accomplishments of the present invention.

DETAILED DESCRIPTION OF THE INVENTION

The present invention is characterized in simple structure, and in utilizing a high pressure air suction activity to draw away the air inside the chamber. Therefore, the present invention is very suitable to a two-dimensional infrared sensor. Below, the embodiments are used to exemplify the thin type vacuum chamber device of the present invention.

Figure 1:
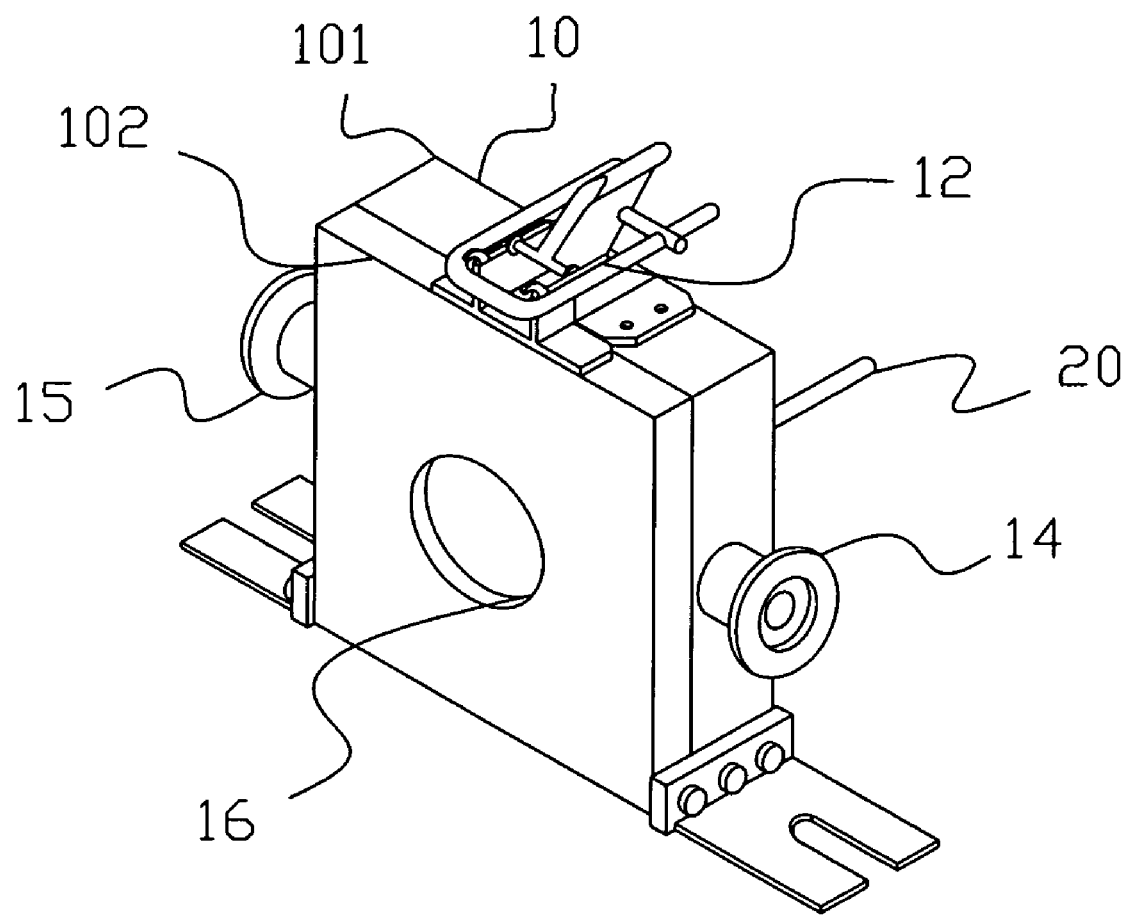
FIG. 1 is a perspective view according to the present invention.

Refer to FIG. 1 a perspective view according to the present invention. The thin type vacuum chamber device of the present invention has a chamber 10 comprising two hollow slabs 101 and 102, which are fastened together by a rotary claw fastener 12. The hollow slab 101 is rotatably coupled to the hollow slab 102 and has the rotary claw fastener 12 to tightly fasten the hollow slab 102, and the chamber 10 is thus airtight. Two rotary spindle valves are respectively arranged at two sides of the chamber 10. The left vacuum spindle valve 15 is an outlet through which the air inside the chamber 10 is pumped out to attain a vacuum state. The right vacuum spindle valve 14 is used in inspecting the vacuum state. A window 16 is arranged on the hollow slab 102, and light or infrared ray can be focused on the object inside the chamber through window 16. The window 16 can reduce the back focal length of the lens of the optical device. An infrared lens may also be mounted on the window 16.

Figure 2:
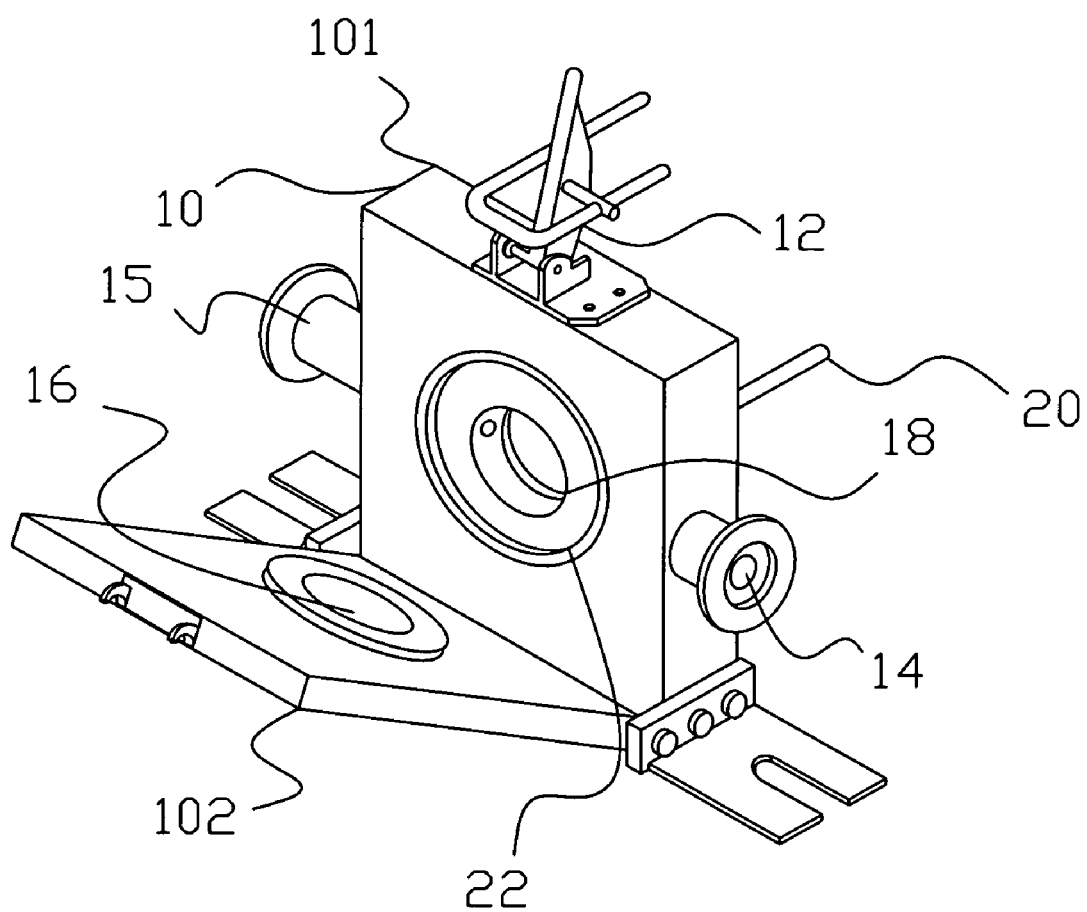
FIG. 2 is another perspective view according to the present invention.

Refer to FIG. 2 another perspective view according to the present invention. The thin type vacuum chamber device of the present invention also has a conduction device 18 and a transmission part 20, and the conduction device 18 is arranged inside the chamber 10. The hollow slab 101 of the chamber 10 has a circular gasket 22, which increases the airtightness of the hollow slabs 101 and 102. The conduction device 18 is connected with the transmission part 20 and sends signals to the external receiving device via the transmission part 20. A sensor may be arranged inside the chamber 10 and closely contacts the conduction device 18; thus, the sensor can be heated or cooled from the exterior. Via the special design of the thin type assembly chamber device, the length of the transmission cable can be effectively reduced, and the signal attenuation and noise interference can also be decreased.

In conclusion, the present invention has the advantage of simple structure. Therefore, the present invention needs only a small installation space and can be conveniently maintained. Thus, the cost is effectively reduced. Besides, the special assembly type design can effectively promote signal quality.

The embodiments described above are only to exemplify the technical contents and characteristics of the present invention to enable the persons skilled in the art to understand, make and use the present invention. However, it is not intended to limit the scope of the present invention. Any equivalent modification or variation according to the spirit of the present invention is to be also included within the scope of the present invention.

What is claimed is:

1. A thin type vacuum chamber device, suitable to a two-dimensional infrared sensor, comprising:

two hollow slabs being rotatable coupled each to the other defining a chamber;

a rotary claw fastener fixedly coupled to an upper surface of each of said slabs tightly fastening said two hollow slabs to form an airtight space;

two rotary spindle valves respectively arranged at two sides of one of said slabs in fluid communication with said chamber, wherein said rotary spindle valve on a first side is used as an outlet through which air inside said chamber is pumped out, and said spindle on a second side is used in inspecting a vacuum state of said chamber;

a window arranged on one said hollow slab allowing light to enter said chamber; and a signal transmission device including a conduction device and a transmission part, wherein said conduction device is arranged inside said chamber, and said transmission part is connected with said conduction device to send signals to an external device.

2. The thin type vacuum chamber device according to claim 1, wherein said window is an optical device.

3. The thin type vacuum chamber device according to claim 2, wherein said optical device is an infrared lens.

4. The thin type vacuum chamber device according to claim 1, wherein a circular gasket is arranged in between said two hollow slabs.

5. The thin type vacuum chamber device according to claim 1, wherein a vacuum-pumping device is connected with one said rotary spindle valve to pump out air via an opening of said rotary spindle valve, and flow rate of pumped air is determined by a size of a connection conduit.

6. The thin type vacuum chamber device according to claim 1, wherein a sensor is arranged inside said conduction device, and said conduction device is used to heat or cool said sensor.

7. The thin type vacuum chamber device according to claim 1, wherein a special assembly design of said signal transmission device, said conduction device, said sensor and said chamber reduces a length of a transmission cable and prevents from signal attenuation and noise interference.

* * * * *